United States Patent [19]

Lindsay et al.

[11] Patent Number: 5,230,702
[45] Date of Patent: Jul. 27, 1993

[54] HEMODIALYSIS METHOD

[75] Inventors: Robert M. Lindsay, London; Brenda L. Skerratt, Aurora, both of Canada

[73] Assignee: Paradigm Biotechnologies Partnership, Toronto, Canada

[21] Appl. No.: 642,285

[22] Filed: Jan. 16, 1991

[51] Int. Cl.⁵ .............................................. A61M 1/16
[52] U.S. Cl. ......................................... 604/4; 604/5; 604/19
[58] Field of Search ............... 604/4, 5, 6, 19, 27, 604/28, 29, 31, 48, 49, 50

[56] References Cited

U.S. PATENT DOCUMENTS

| | | | |
|---|---|---|---|
| 3,910,256 | 10/1975 | Clark et al. | 604/4 X |
| 4,231,366 | 11/1980 | Schael. | |
| 4,526,568 | 7/1985 | Clemens et al. | 604/28 X |
| 4,718,891 | 1/1988 | Lipps | 604/31 |
| 4,897,184 | 1/1990 | Shouldice et al. | |
| 4,940,455 | 7/1990 | Guinn | 604/5 |
| 4,967,754 | 11/1990 | Rossi | 604/5 X |

FOREIGN PATENT DOCUMENTS

| | | |
|---|---|---|
| 358873 | 7/1989 | European Pat. Off. |
| 2624384 | 12/1976 | Fed. Rep. of Germany. |
| 3436748 | 7/1985 | Fed. Rep. of Germany. |

OTHER PUBLICATIONS

Gotch and Sargent, *Kidney International*, 28: 526-534 (1985).
Jindal et al, *Trans. Am. Soc. Artif. Intern. Organs*, 33: 286-288 (1987).
Daugirdas, *Trans. Am. Soc. Artif. Intern. Organs*, 35: 336-338 (1989).
Lindsay et al, *Kidney International*, vol. 33 suppl 24: S-92-S99 (1988).

*Primary Examiner*—Robert A. Hafer
*Assistant Examiner*—Sam Rimell
*Attorney, Agent, or Firm*—Timothy R. Kroboth

[57] ABSTRACT

A dialysis method based upon urea kinetic analysis is provided. An objective of the method is to provide guaranteed dose hemodialysis by optimization of each dialysis treatment. The method does not rely upon dialysis treatments equal in time. The method includes determining a preferred post-dialysis urea concentration for a patient and predicting a time endpoint for the dialysis. Computer automation makes the method advantageous in a large, busy dialysis center.

14 Claims, 1 Drawing Sheet

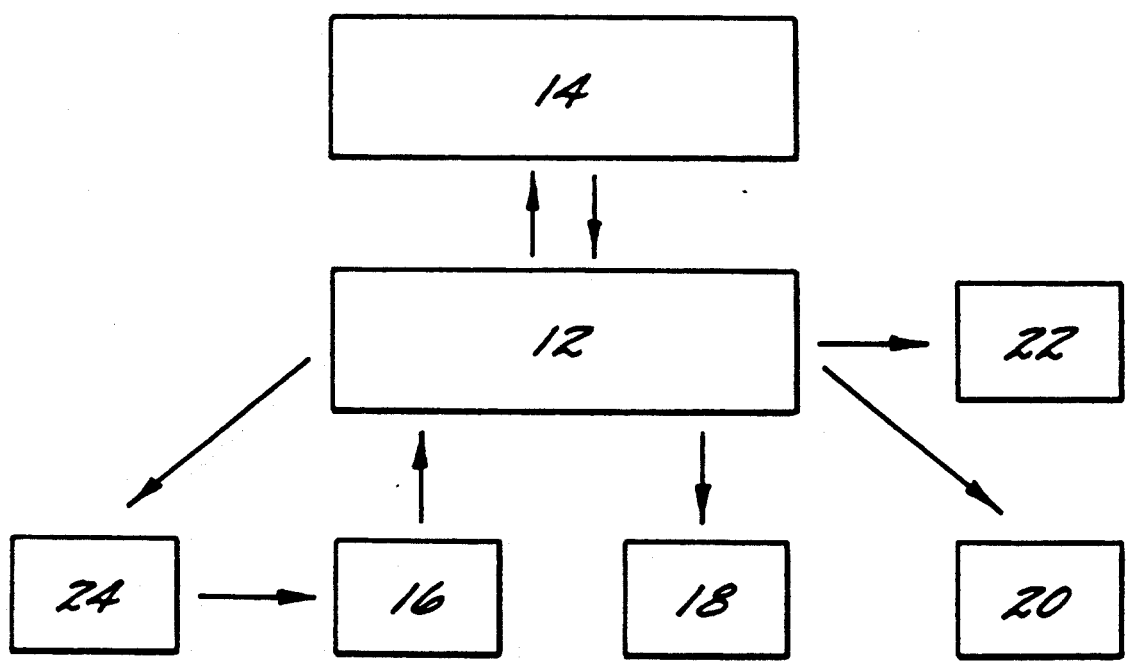

HEMODIALYSIS METHOD

BACKGROUND OF THE INVENTION

This invention relates to the field of hemodialysis.

The life expectancy of patients with irreversible renal failure can be prolonged by hemodialysis using an extracorporeal circuit including a dialyzer (or artificial kidney). As there is no specific measurable toxin in the blood of such patients, the provision of a "dose" of treatment has been, for the most part, trial and error. A physician bases the dialysis prescription often empirically, or if on some concept, on for instance, the effect on patient well-being or on blood levels of waste such as creatinine or urea. Currently, the hemodialysis procedure for patients with end stage renal failure involves treatment three times per week for three to six hours, with the majority of patients in North America being dialyzed for four hours or less.

The lack of understanding of the pathogenesis of uremia has made it difficult, and continues to make it difficult, to clearly define an adequate dialysis prescription. Because of a dispute over which uremic toxins were important and because of the clear need for a quantifiable approach for the dialysis prescription, the National Cooperative Dialysis Study (NCDS) was undertaken in the 1970's and has been a source of continual review since its publication in the 1980's.

At any point in time during dialysis, the blood concentration of urea depends on its rate of generation, its volume of distribution, the residual renal function, the clearance of the dialyzer, and the elapsed dialysis time. The clearance of the dialyzer will depend upon the nature of the membrane, the effective membrane surface area, the blood flow rate, and the dialysate flow rate.

The normalized dose of dialysis can be defined for urea by the dimensionless parameter $Kt/V$, where $K$ is the clearance of urea by the dialyzer (ml/min), where $t$ is time (min.), and where $V$ is the volume of distribution of urea (ml). Current methods of calculating $Kt/V$ (urea) are complex and require accurate measurement of the dialyzer urea clearance and subsequent calculation of the volume of distribution of urea. The only accurate way of determining the dialyzer urea clearance and volume of urea distribution is to collect the total dialysate and assay the urea content, and the logistic problems of this approach prevent its general use.

One study involving a mechanistic analysis of the NCDS data has indicated that the probability of uremic manifestations is high (57%) and constant over the treatment range $0.4 \leq Kt/V$ (urea) $\leq 0.8$, and that over the treatment range $0.9 < Kt/V$ (urea) $< 1.5$, there is a sharp decrease in morbidity to a constant 13%. Other studies have confirmed that a $Kt/V$ (urea) of 1 or more should be targeted.

However, each dialysis is not equal. Patients may not receive the prescribed $Kt/V$ (urea) for various reasons including decrease in blood pressure and decreased blood flow rates.

Work by Jindal and co-workers utilizes the equation $Kt/V = 0.04 \, PRU - 1.2$, and has indicated that a percent reduction in blood urea concentration (PRU) of approximately 55 during hemodialysis is necessary to obtain a $Kt/V$ (urea) of 1. More recently, Daugirdas has argued that the PRU may result in $Kt/V$ (urea) values substantially above or below the target $Kt/V$, and suggested the formula $Kt/V = -\ln(R - 0.03 - UF/W)$, where $R$ is the post/predialysis plasma urea ratio, where 0.03 is a constant that allows for urea generation during dialysis, where UF is the prescribed ultrafiltration volume (1) over dialysis, and where W is the prescribed post-dialysis weight (kg).

Increasing numbers of nephrologists are using various methodologies for calculating $Kt/V$ (urea) as a basis for the dialysis prescription. However, at present, few renal units are using any form of urea kinetics to aid in the dialysis prescription, and a recent study shows that even in a dialysis unit using urea kinetic modelling on a regular basis, the prescribed dose of dialysis $Kt/V$ is frequently not achieved.

Furthermore, in this current time of economic restraint, there is pressure upon health care teams to consider cost efficiency in therapeutic strategies. To the nephrologist, this may mean shortening dialysis time by using a device "more efficient" in removing uremic toxins.

As illustrated by U.S. Pat. Nos. 4,231,366 to Schael and 4,897,184 to Shouldice et al, computer automation of hemodialysis has been considered in which sensor signals are inputted to a control circuit, condition control is effected, conditions are monitored to be within a predetermined limit, and a failure to be within the limit is signalled. Schael uses this automated approach to maintain patient blood flow within predetermined limits, due to the effect of blood flow on time for dialysis. However, computer automation has not been employed to predict a time endpoint for dialysis.

Accordingly, there is a need for an improved hemodialysis method based upon urea kinetics. Advantageously, the method would provide guaranteed dose hemodialysis, that is, would target the optimization of each dialysis treatment and no longer rely upon dialysis treatments equal in time as in the Schael approach. Beneficially, the improved hemodialysis method would provide cost savings. Preferably, the method would be automated and could predict a time endpoint for dialysis. If so, better scheduling of patients would result.

SUMMARY OF THE INVENTION

It is accordingly an object of the present invention to provide an improved method for hemodialysis based upon urea kinetic analysis.

It is a further object to provide a hemodialysis method in which optimization of each dialysis treatment is targeted, and which would no longer rely upon dialysis treatments equal in time.

It is a still further object to provide a dialysis method which will provide cost savings.

It is an even further object to provide an automated dialysis method that will predict a time endpoint for dialysis.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, there is provided an improved dialysis method based upon urea kinetic analysis.

The method requires measuring urea concentration, suitably the blood urea concentration of the dialysis patient. Urea concentration may also be measured on the dialysate side. Typically, at least three measurements of urea concentration are made. An initial measurement is suitably made immediately after beginning dialysis.

A preferred post-dialysis urea concentration is determined. A value for Kt/V (urea) in the range of about 0.8 to 1.4 is appropriate for the determination, where K is the dialyzer urea clearance (mls/minutes), where t is time (minutes) and where V is volume of distribution for urea (mls). The Kt/V (urea) value is typically selected by the physician.

An essential feature of the method is that a time endpoint for dialysis is predicted. The endpoint prediction is based upon the preferred post-dialysis urea concentration and measured urea concentration values.

Urea concentration is measured at about the predicted time endpoint, and the urea concentration value obtained is compared with the preferred post-dialysis urea concentration. If appropriate, dialysis should be terminated.

In the detailed description of the invention that follows, there is essentially described only a preferred embodiment of this invention, simply by way of illustration of the best mode contemplated of carrying out this invention. As will be realized, this invention is capable of other and different embodiments, and its several details are capable of modification in various respects, all without departing from the invention. Accordingly, the detailed description is to be regarded as illustrative in nature, and not as restrictive.

BRIEF DESCRIPTION OF THE DRAWING

Reference is now made to the accompanying drawing, which forms a part of the specification of the present invention, and which is a block diagram depicting a preferred automated approach for carrying out a dialysis method in accordance with the present invention.

DETAILED DESCRIPTION OF THE INVENTION

The present invention is an improved hemodialysis method based upon urea kinetics. Advantageously, the method, which may be called guaranteed dose hemodialysis (GDHD), targets the optimization of each dialysis treatment, and no longer relies upon dialysis treatments equal in time. Beneficially, the improved hemodialysis method of the present invention provides cost savings. Preferably, the method uses computer automation to predict a time endpoint for dialysis. As will become clear, the improved hemodialysis method of the present invention provides for better scheduling of patients.

The method is now described with reference to an embodiment in which blood urea concentration, more specifically, concentration of urea in the plasma water, is measured. However, urea concentration could be measured on the dialysate side. The urea concentration is more dilute in the dialysate fluid than in the plasma water.

In the method of the present invention, an initial measurement of the urea concentration is made, suitably immediately after commencing dialysis of the patient. To this end, the patient's blood may be sampled and the urea concentration of the blood sample may be measured. This step can be achieved through conventional technology.

In the method of the present invention, it is essential that a preferred post-dialysis urea concentration be determined for the patient. The determination is advantageously based upon the dimensionless parameter Kt/V (urea), which was earlier described in the Background portion of this description of the present invention. More specifically, the requisite blood urea value may be determined for the patient from the initial blood urea concentration and a value for the proportion of blood urea remaining (R) calculated based upon Kt/V (urea). In short, the preferred post-dialysis blood urea concentration may be calculated as the mathematical product of the initial blood urea concentration and R, or $(1-PRU/100)$. R equals $1-PRU/100$, where PRU, as earlier explained, is the percent reduction in blood urea.

It has been found that the proportion of blood urea remaining (R) is beneficially calculated using the formula $$R = 1 - [(Kt/V + 1.2)/4 + UGEN + (UF/IDWT)],$$

where a value for Kt/V is in the range of about 0.8 to 1.4, with a value greater than or equal to about 1.0 being typically advantageous. UGEN is suitably a constant of about 0.03 that allows for urea generation during dialysis. UF is the volume (liters) of ultrafiltrate to be lost by the patient during dialysis. IDWT is the patient ideal weight (Kg). The values for Kt/V, UF and IDWT will typically be physician prescribed. Typically, it has been found that optimization of dialysis results when R is less than 0.45, particularly when R is in the range of about 0.4 to 0.35.

In the method of the present invention, urea concentration is measured at two or more subsequent time intervals, typically at about 60 and 120 minutes of dialysis. A suitable additional measuring time is at 180 minutes of dialysis. These urea concentration measurements are made in a manner similar to the initial measurement.

As an essential feature of the method of the present invention, a time endpoint for dialysis is predicted. This feature of the present invention provides for cost savings compared to the use of dialysis treatments equal in time. The predicted time endpoint may result in about 30 to 80 minutes of dialysis time being saved. In such case, dialysis cost to the patient will be reduced, and the dialysis center is also benefitted because it can more efficiently handle the patient load.

In a preferred embodiment, the prediction of the time endpoint is conveniently achieved using a linear relationship between proportion of blood urea remaining and time based upon the prior readings of blood urea concentration. The linear relationship may be determined by plotting the prior readings on a graph having axes of time (minutes) and proportion of blood urea remaining. The proportion of blood urea remaining is beneficially graphed as a logarithmic equivalent, which may be a natural logarithmic equivalent. The time endpoint for dialysis is the time coordinate of the intersection of the value of the ratio of the preferred post-dialysis blood urea concentration to the initial blood urea concentration, with the linear plot. Alternatively, as will be described, an algorithm based upon linear regression analysis may be used for predicting the time endpoint for dialysis.

In the method of the present invention, urea concentration is measured at about the predicted time endpoint and compared with the preferred post-dialysis urea concentration. The urea concentration measurement is made in a manner similar to the initial urea measurement, and the necessary comparison is made.

If the comparison reveals that the preferred post-dialysis blood urea concentration has been obtained or substantially obtained or has been exceeded, with a deviation of about $+/-10\%$ generally being within the objective, dialysis should be terminated. On the other hand, if the comparison reveals that further dialysis is appropriate, then a revised time endpoint for dialysis should be predicted, and the urea concentration at that revised endpoint compared with the preferred post-dialysis blood urea concentration.

If desired or appropriate for enhanced accuracy of the method, third and even subsequent measuring times can be predicted prior to predicting the time endpoint. The prediction may be made by using the prior measurements of urea concentration either to graphically determine a linear relationship between proportion of urea remaining and time, or to conduct a linear regression analysis. Further measurements of urea concentration are thereafter made, and the results are used to predict a time endpoint for dialysis.

The method of the present invention is well suited for a large, busy dialysis center. Patient identifying information, the desired values for Kt/V, UF and IDWT for the particular patient, urea concentration measuring times, and urea concentration data may be beneficially inputted to a computer system equipped with appropriate software.

Referring to the FIGURE, a suitable computer system includes a conventional microprocessor 12 and a conventional programmable memory 14, which operatively intercommunicate. In a preferred automated approach, urea concentration data may be automatically inputted to the microprocessor by conventional equipment 16 for analyzing urea-containing fluid samples, so that the method provides for measuring the removal of urea on-line during dialysis.

Based on the inputted data, the computer microprocessor advantageously determines the preferred post-dialysis urea concentration and predicts a time endpoint for dialysis, or may predict a third and even subsequent urea concentration measuring times and then predict a time endpoint based upon the urea concentration measurements. In any event, microprocessor 12 generates a signal indicative of the preferred post-dialysis urea concentration or a signal indicative of a time, and communicates the same to programmable memory 14. The programmable memory receives and stores the signals.

An algorithm for predicting a time endpoint for dialysis may be stored in memory 14. A suitable algorithm is based upon a linear regression of the curve for the decreasing urea concentration during dialysis. For four blood urea concentrations, the algorithm may be as follows:

1. Take four urea concentrations (representing four different sampling times): $c_0$, $c_1$, $c_2$ and $c_3$.

2. Non-dimensionalize each concentration by dividing each $c_n$ by $c_0$ to yield $C_n$ (or the proportion of blood urea remaining).

3. Also non-dimensionalize the preferred post-dialysis blood urea concentration ($c_{ep}$) by dividing $c_{ep}$ by $c_0$, so that if $c_{ep}$ is 5 and $c_0$ is 40, then $C_{ep} = 5/40 = 0.125$.

4. Determine the linear constant using the equation for a regression slope for a line through the origin, which equation is $b = [\text{sum of } (X_n \times \ln C_n)]/(\text{sum of } X_n^2)$ a) Compute the sum of the square of each time $X_n$ (minutes) at which the samples were taken, that is, the sum of $X_0^2$, $X_1^2$, $X_2^2$ and $X_3^2$, so that if the samples were taken at 0, 60, 120 and 180 minutes, then $0^2 + 60^2 + 120^2 + 180^2 = 50{,}400$.

b) Calculate the sum of the product of time ($X_n$) and $\ln C_n$ (natural logarithmic value of the proportion of urea remaining) at the respective time, for the four samples, that is, if the urea concentrations of the four samples are 40, 30, 20 and 10, then $[0 \times \ln (40/40)] + [60 \times \ln (30/40)] + [120 \times \ln (20/40)] + [180 \times \ln (10/40)] = -349.97$.

c) Solve the foregoing equation for b using the illustrative values of a) and b) above, such that $b = -349.97/50{,}400 = -0.00694$.

5. Calculate the predicted time endpoint for dialysis using the linear relation $Y = bX$ and $Y_{ep} = \ln C_{ep}$, such that when $C_{ep} = 0.125$ and b has the illustrative value of 4.c) above, then $\ln C_{ep} = -2.079$; and $X_{ep} = Y_{ep}/b = -2.079/-0.00694 = 299$ minutes.

If desired, the computer could activate an audible or visual signal to indicate a urea concentration measuring time. In such case, programmable memory 14 automatically communicates at the appropriate time with microprocessor 12, which in turn, as represented in the FIGURE, may activate a signal light 18 to indicate the time.

The urea concentration at about the predicted time endpoint for dialysis is compared by the microprocessor with the preferred post-dialysis urea concentration. If desired, the computer could cause an audible or visual signal to be given to indicate, if appropriate, termination of dialysis. In such case, microprocessor 12 may activate a signal light 20, which may be green, to indicate termination of dialysis.

In the event the comparison reveals that further dialysis is appropriate, the microprocessor beneficially may predict a revised time endpoint for dialysis, and thereafter compare the urea concentration at the revised time endpoint with the preferred post-dialysis blood urea concentration.

Beneficially, microprocessor 12 communicates with a conventional printer 22, which provides a paper record in the form of, for instance, a graph of proportion of blood urea remaining and time. A paper record would assist the physician in evaluation of the patient.

In a highly automated embodiment of the method of the present invention, computer control of urea-containing fluid sampling may be provided. In such case, signals indicative of selected measuring times such as 0 time, 60 minutes and 120 minutes, are stored in programmable memory 14. At a selected time, the programmable memory automatically communicates with the microprocessor, which in turn activates a fluid sampling device 24. Thus, a technician would need only to commence and terminate dialysis, and input necessary data.

Accordingly, by the method of the present invention, optimization of each dialysis treatment is targeted, rather than targeting dialysis treatments equal in time. The improved hemodialysis method provides cost savings and provides for better scheduling of patients. While the method has been described primarily with reference to blood side measurements and values, urea could be also measured on the dialysate side.

EXAMPLE

A blood sample of a patient is taken immediately after commencing dialysis, and a blood urea concentration of 17.4 mmol/L found and inputted to microprocessor 12. Physician-prescribed values for the patient are 1.0 for the Kt/V, 3 liter for the volume of ultrafiltrate to be lost during dialysis, and 72 kg for the ideal weight. These values are likewise inputted to microprocessor 12, which uses these values and a value of 0.03 mmol for UGEN, in the formula $$R=1-(Kt/V+1.2)/4+UGEN+(UF/IDWT)],$$

to calculate a value of 0.38 for the proportion of blood urea remaining. Thereafter, the computer calculates a preferred post-dialysis blood urea concentration of 6.6 mmol (the mathematical product of 17.4 mmol and 0.38).

Thereafter, blood samples are taken at 60 min and 120 min, and blood urea concentrations of 12.2 mmol and 9.0 mmol are found. These values of blood urea concentration and time are inputted to microprocessor 12, which predicts a time endpoint for the dialysis.

A blood sample is taken at the predicted time endpoint, and the blood urea concentration at such time is found to be 6.8 mmol. This value is inputted to microprocessor 12, which compares the value to the preferred value of 6.6. Microprocessor 12 activates green signal light 20 to indicate that dialysis may be terminated.

Having described the invention in detail and by reference to a preferred embodiment thereof, it will be apparent that modifications and variations are possible without departing from the scope of the invention defined in the appended claims. Several changes or modifications have been briefly mentioned for purposes of illustration.

We claim:

1. A dialysis method based upon urea kinetic analysis, said method comprising measuring urea concentration, determining a preferred post-dialysis urea concentration from an initial urea concentration and a value for the proportion of urea remaining based upon a prescribed value for Kt/V, where K is the dialyzer urea clearance (mls/minutes), where t is time (minutes) and where V is volume of distribution for urea (mls), predicting a time endpoint for dialysis based upon said preferred post-dialysis urea concentration, and upon measured urea concentration values and the respective times of dialysis, measuring urea concentration at about said predicted time endpoint, and comparing the urea concentration at about said predicted time endpoint with said preferred post-dialysis urea concentration to determine whether the prescription has been satisfied.

2. The dialysis method of claim 1, further comprising when said comparing reveals that further dialysis is appropriate, predicating a revised time endpoint for dialysis based upon said preferred post-dialysis urea concentration, and upon measured urea concentration values and the respective times of dialysis, measuring urea concentration at about said revised time endpoint, and comparing the urea concentration at about said revised time endpoint with said preferred post-dialysis urea concentration.

3. The dialysis method of claim 1, further comprising prior to predicting said time endpoint, predicting a time for measuring urea concentration, and measuring urea concentration at about said predicted time.

4. The dialysis method of claim 1, wherein the urea concentration measurements are on the blood side.

5. The dialysis method of claim 1, wherein the urea concentration measurements are on the dialysate side.

6. The dialysis method of claim 1, wherein said value for Kt/V is greater than or equal to about 1.

7. The dialysis method of claim 1, wherein said determining of said preferred post-dialysis urea concentration is carried out by a microprocessor based upon values inputted to said microprocessor.

8. The dialysis method of claim 1, wherein said predicting of said time endpoint is carried out by a microprocessor based upon values inputted to said microprocessor.

9. The dialysis method of claim 1; wherein said comparing is conducted by a computer microprocessor based upon values inputted to said microprocessor.

10. The dialysis method of claim 8, wherein said microprocessor directs that a signal be given to indicate a time for measuring urea concentration.

11. The dialysis method of claim 9, wherein said microprocessor directs, after carrying out said comparing, that a signal be given to indicate that dialysis may be terminated.

12. An automated dialysis method based upon urea kinetic analysis, said method comprising measuring urea concentration in response to a microprocessor-activated signal; effecting a microprocessor-based determination of a preferred post-dialysis urea concentration from an initial urea concentration and a value for the proportion of urea remaining based upon a value for Kt/V, where K is the dialyzer urea clearance (mls/minutes), where t is time (minutes) and where V is volume of distribution for urea (mls); effecting a microprocessor-based prediction of a time endpoint for dialysis based upon said preferred post-dialysis urea concentration, and upon measured urea concentration values and the respective times of dialysis; measuring urea concentration at about said predicted time endpoint; and carrying out a microprocessor-based comparison of the urea concentration at about said predicted time endpoint with said preferred post-dialysis urea concentration.

13. The dialysis method of claim 12, wherein the urea concentration measurements are on the blood side.

14. The dialysis method of claim 12, wherein the urea concentration measurements are on the dialysate side.

* * * * *